United States Patent [19]

Bowers et al.

[11] Patent Number: 4,802,485

[45] Date of Patent: Feb. 7, 1989

[54] SLEEP APNEA MONITOR

[75] Inventors: David L. Bowers, La Mesa; Gunther W. Kienle, El Cajon, both of Calif.

[73] Assignee: Sentel Technologies, Inc., Waukesha, Wis.

[21] Appl. No.: 92,055

[22] Filed: Sep. 2, 1987

[51] Int. Cl.$^4$ .............................................. A61B 5/00
[52] U.S. Cl. .................................. 128/633; 128/637; 128/670
[58] Field of Search ............... 128/709, 670, 700, 725, 128/633, 637, 644, 671

[56] References Cited

U.S. PATENT DOCUMENTS

| | | | |
|---|---|---|---|
| 1,619,005 | 3/1927 | Strong | 128/671 |
| 3,998,213 | 12/1976 | Price | 128/644 |
| 4,321,930 | 3/1982 | Jobsiso et al. | 128/633 |
| 4,359,726 | 11/1982 | Lewiner et al. | |
| 4,509,527 | 4/1985 | Fraden | |
| 4,700,708 | 10/1987 | New, Jr. et al. | 128/633 |

OTHER PUBLICATIONS

"Vitalog PMS-8".
"Kynar Piezo Film Technical Manual", pp. 1–26, Pennwalt Corporation Copyright 1983.
"Watch Bird Apnea Monitor", Bernard DeBerry, M.D., F.A.C.S., pp. 1–3.
"Sleep Apnea Syndromes", Circle Reader Service Card No. 37-40, Respiratory Therapy, Jan./Feb. 1981, 1981 Barrington Publications, Inc.
"Piezo Film Sensors", The Journal of Machine Perception, May 1986, vol. 3, No. 5.
"Kynar Piezo Film", published by Pennwalt Corporation.
"Obstructive Sleep Apnea", Symposium on Sleep Disorders, Colin E. Sullivan, (Med. A.M.B. B.S., Ph.D. F.R.A.C.P. and Faiq G. Issa, M.B., B.S. Ph.D.
"Analysis of Apnea in Sleep Apnea", by David Kurtz and Jean Krieger 1978 Alan R. Liss, Inc.

Primary Examiner—William E. Wayner
Attorney, Agent, or Firm—Willian Brinks Olds Hofer Gilson & Lione Ltd.

[57] ABSTRACT

A sleep apnea monitor includes an $SaO_2$ sensor, a breathing sensor, a snoring sensor, and a head position sensor, all of which are mounted to a headgear. The breathing sensor preferably includes a piezo-electric film formed of a generally cylindrical shape positioned between the nose and mouth of the subject such that exhaled air warms the film and generates an electric signal indicative of the brathing pattern of the subject. Preferably, the region bounded by the piezo-electric film is used as a resonant cavity which is acoustically coupled to a microphone included in the snoring sensor. In one embodiment, data is logged from the sleep apnea monitor at the rate of one measurement for each pulse beat of the subject. In this way, data recording is synchronized with a physiological variable.

17 Claims, 9 Drawing Sheets

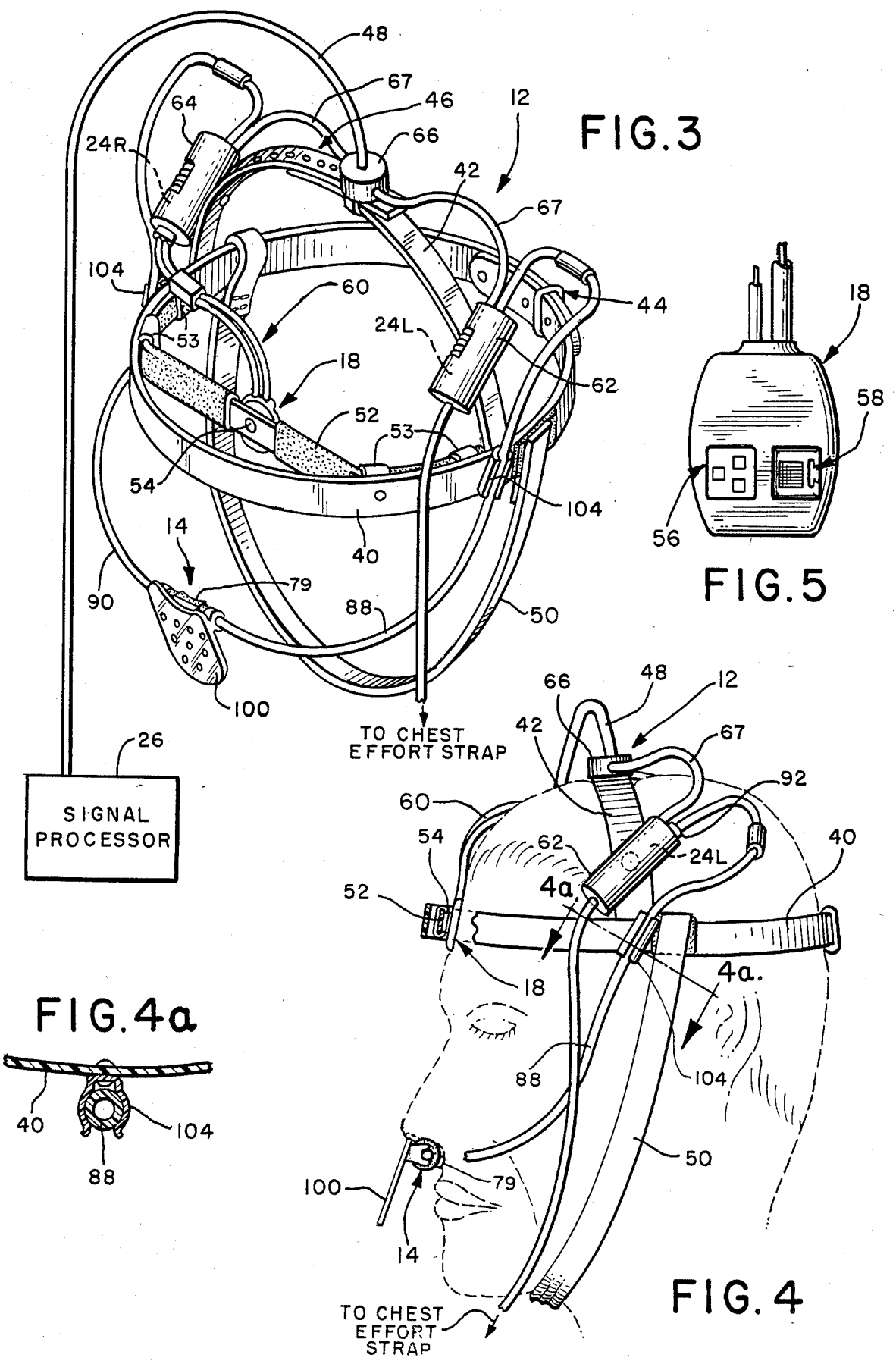

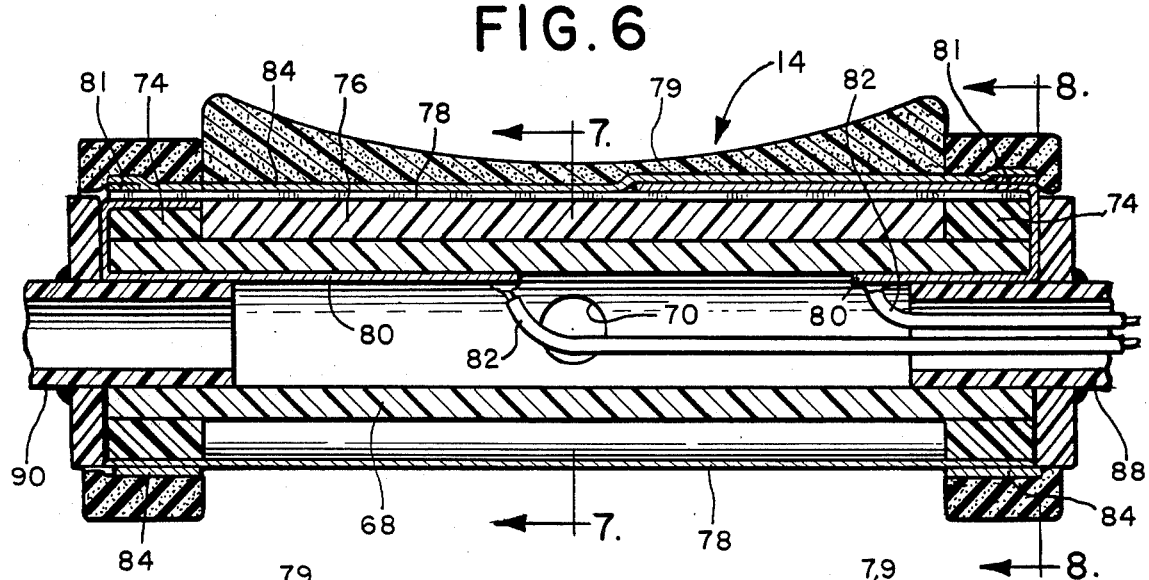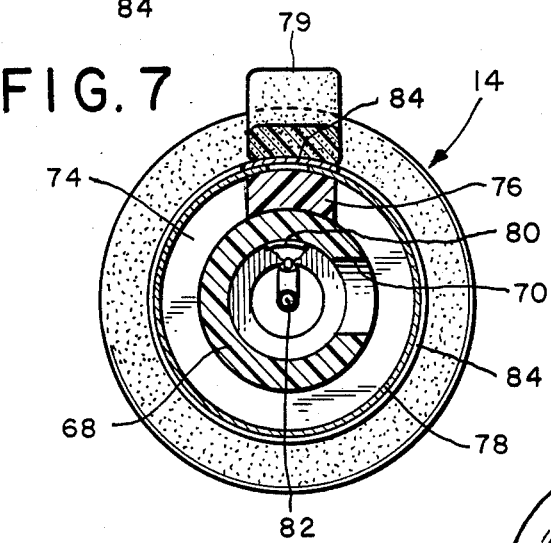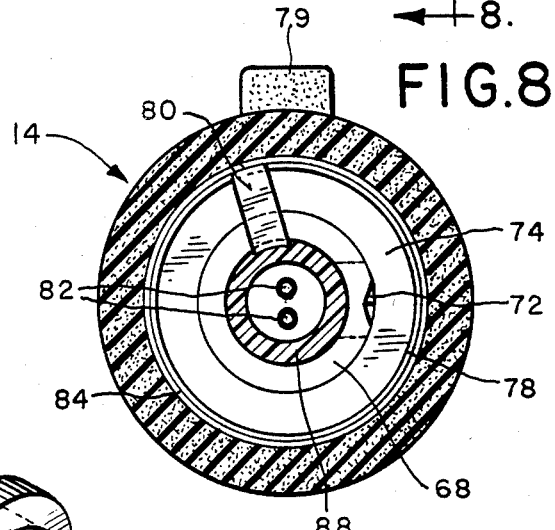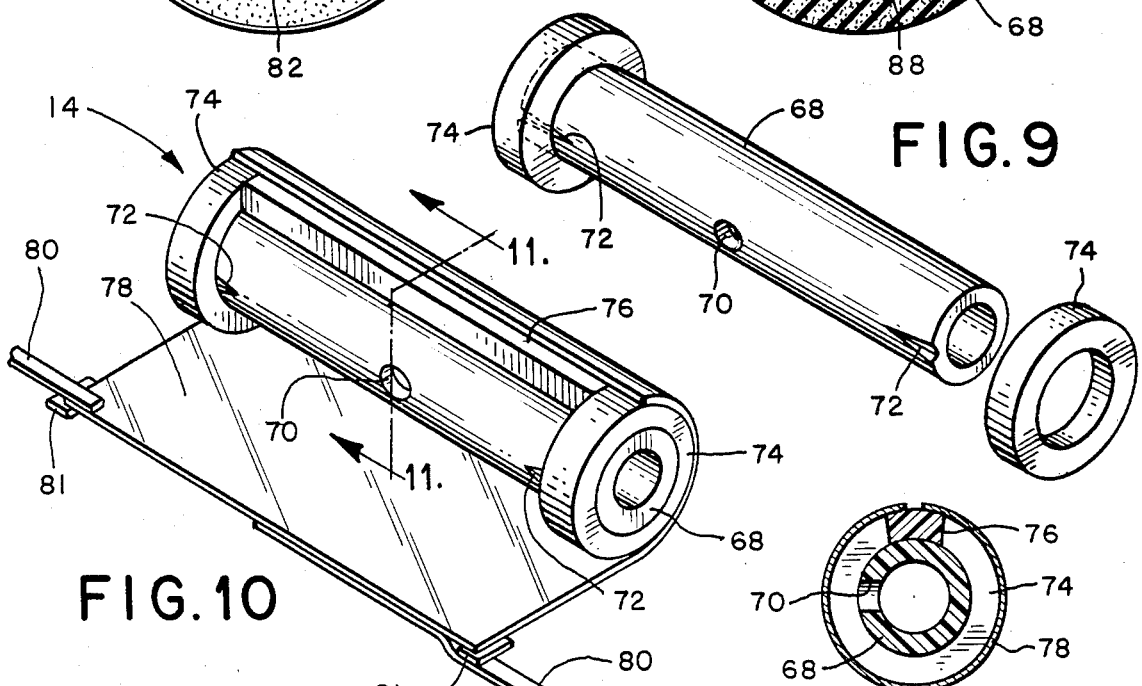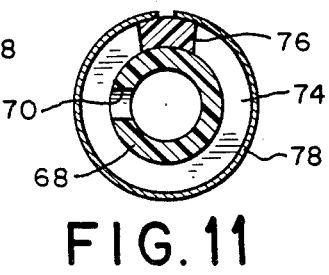

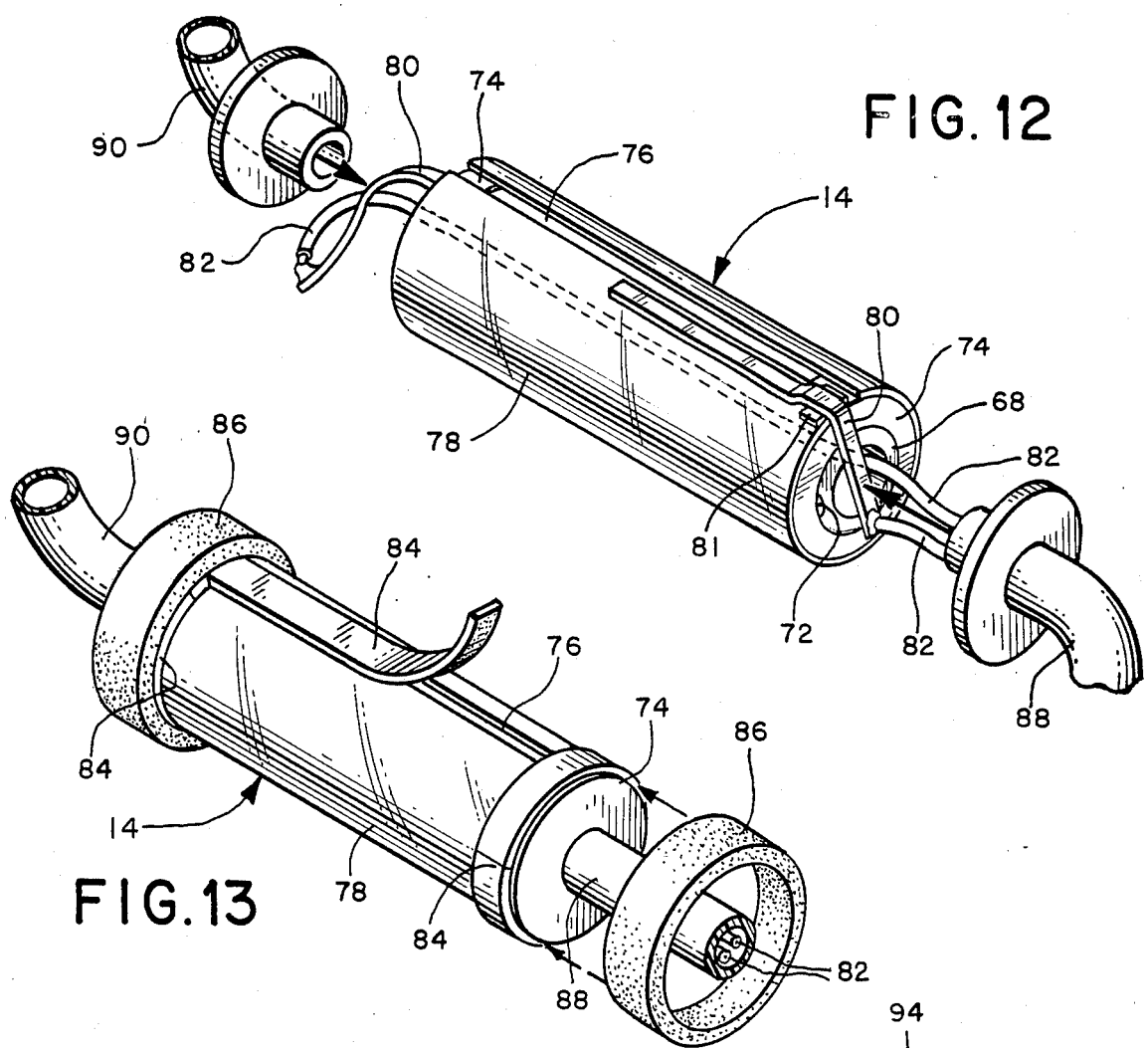
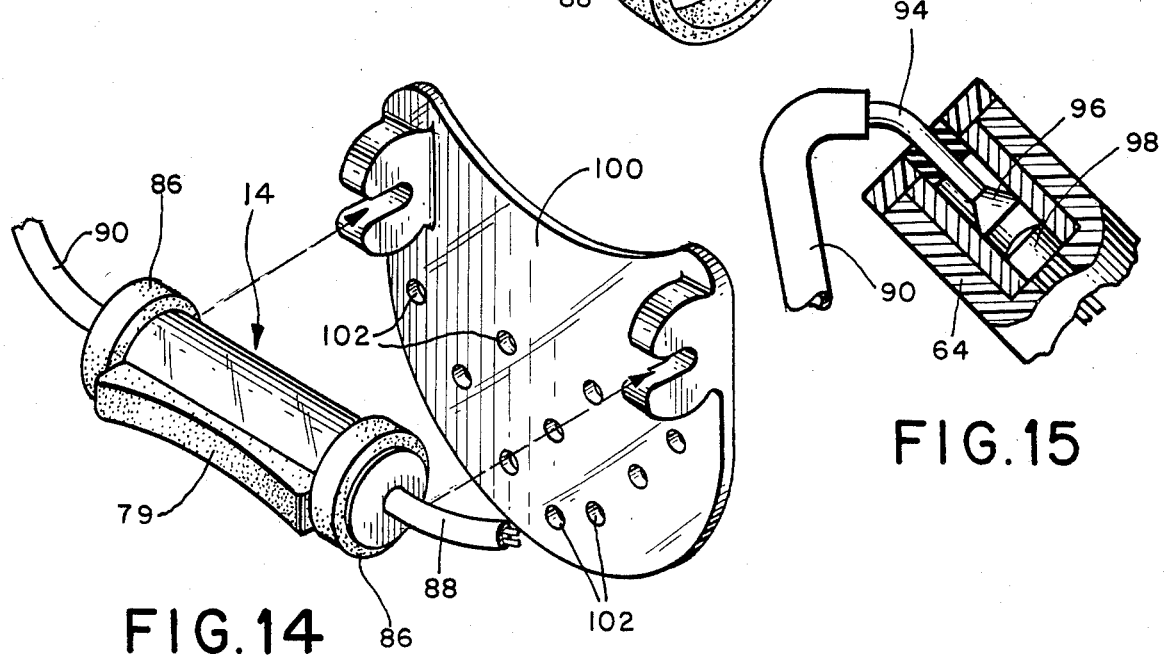
FIG. 12
FIG. 13
FIG. 14
FIG. 15

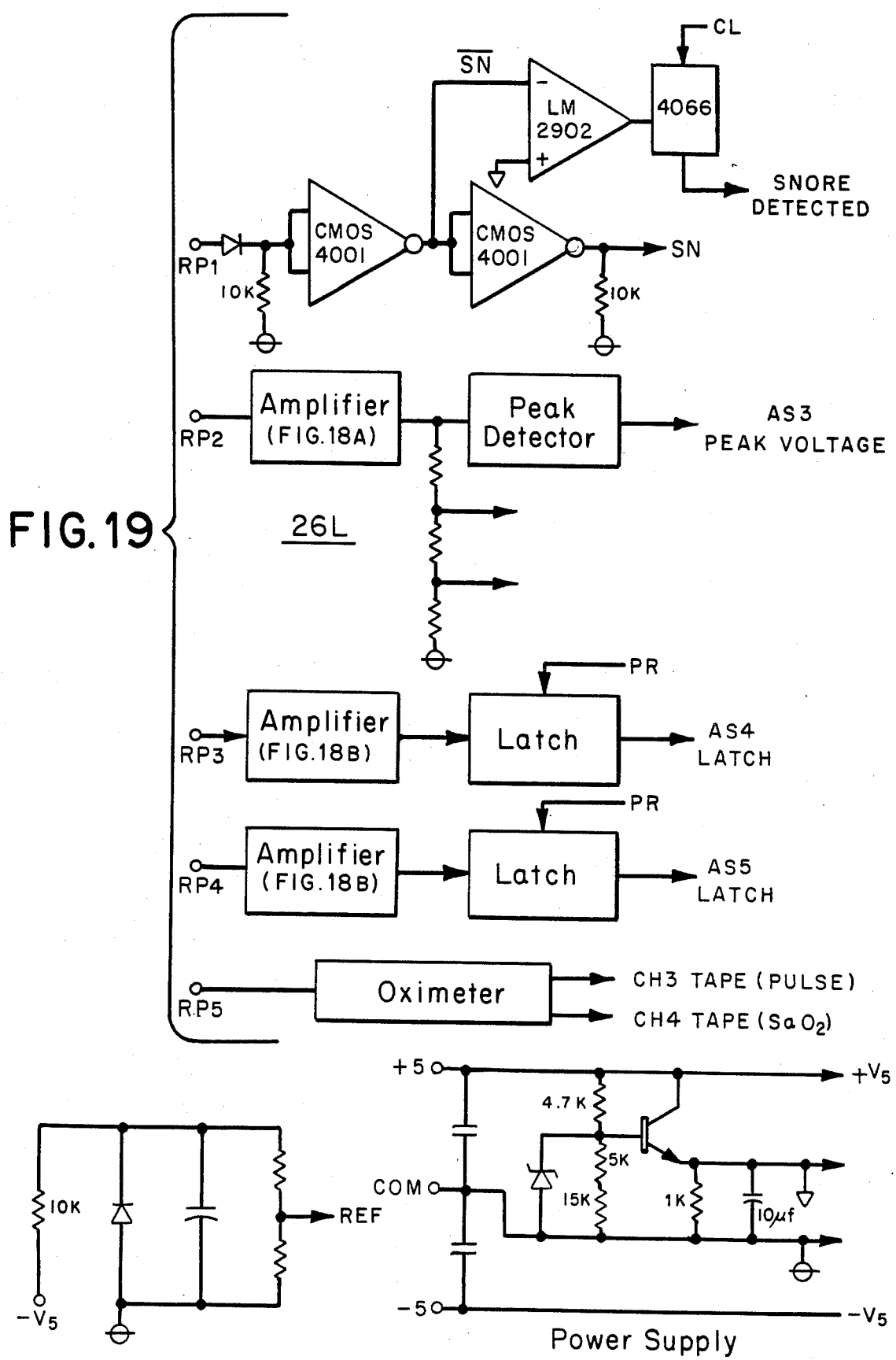

SLEEP APNEA MONITOR

BACKGROUND OF THE INVENTION

The present invention is related to equipment for monitoring health parameters such as breathing pattern, chest motion, snoring pattern, and oxygen saturation ($SaO_2$) levels of a subject. Such parameters can be important diagnostic aids in detecting and diagnosing sleep apnea.

Sleep apnea is characterized by an interruption in breathing that reduces $SaO_2$ levels. A significant fraction of the population suffers from sleep apnea, and a need exists for an improved screening monitor to diagnose sleep apnea events accurately.

An important objective of this invention is to provide an improved sleep apnea monitor which can be adjusted to fit a specific subject in a reduced amount of time, which reliably measures the desired parameters (preferably in the home with no supervision), which is convenient to use and to wear by the subject, which requires no calibration or warm up time, and which reliably positions the individual sensors so as to insure repeatable results in subsequent monitoring periods.

SUMMARY OF THE INVENTION

The improved monitoring system of this invention is defined by the following claims. As will become apparent from the following detailed description, the sleep apnea monitor described below utilizes a head strap which positions the majority of the sensors about the head of the subject. $SaO_2$ is measured from the forehead of the subject, and snoring and breathing patterns are measured with a sensor positioned between the nose and the mouth of the subject. It has been found that this arrangement of monitors allows the sensors to be adjusted quickly and reliably for individual subjects. Furthermore, since the head gear described below can readily be removed and repositioned by the subject, the pre-adjusted sensors can readily be returned to their desired sensing positions.

The monitoring device described below includes a breath sensor that utilizes a piezo-electric film formed in a cylindrical shape. Exhaled air from the subject warms the film, producing a characteristic voltage signal which is processed by the monitor as an indication of breathing pattern. Furthermore, the film forms a wall of a resonant chamber that is acoustically coupled to a microphone. The sounds and vibrations associated with snoring are selectively passed to the microphone and are monitored by the microphone as an indication of the snoring pattern of the subject. This approach has been found to provide excellent discrimination between snoring and speech. Because the breath sensor is combined with portions of the snoring sensor, the bulk and complexity of the monitor are reduced.

Another important feature is that data obtained from the sensors can be logged or recorded at periodic intervals which are synchronized with the heart pulse of the subject. In one of the monitors described below, one set of sensor signals is recorded at each heartbeat of the subject. By correlating the recorded sensor readings with the heartbeat of the subject more consistent, physiologically significant results are obtained.

The invention itself, together with further objects and attendant advantages, will best be understood by reference to the following detailed description, taken in conjunction with the accompanying drawings.

BRIEF DESCRIPTION OF THE DRAWINGS

FIG. 3 is a perspective view of the headgear included in the monitors of FIGS. 1 and 2.

FIG. 4 is a side view of the headgear of FIG. 3 in use.

FIG. 4a is a sectional view taken along line 4a—4a of FIG. 4.

FIG. 5 is a partial plan view of the oximetric sensor included in the headgear of FIGS. 3 and 4.

FIG. 6 is a longitudinal sectional view through the breath sensor of the headgear of FIGS. 3 and 4.

FIG. 7 is a sectional view taken along line 7—7 of FIG. 6.

FIG. 8 is a sectional view taken along line 8—8 of FIG. 6.

FIGS. 9–14 are various views of the breath sensor of FIG. 6 in progressive stages of assembly.

FIG. 15 is a detailed view in partial section of portions of the snoring sensor of the headgear of FIG. 3.

FIGS. 18, 18A–18E, 19, 19A and 19B are circuit diagrams of the signal processor of FIG. 1.

DETAILED DESCRIPTION OF THE PRESENTLY PREFERRED EMBODIMENTS

Figure 1:
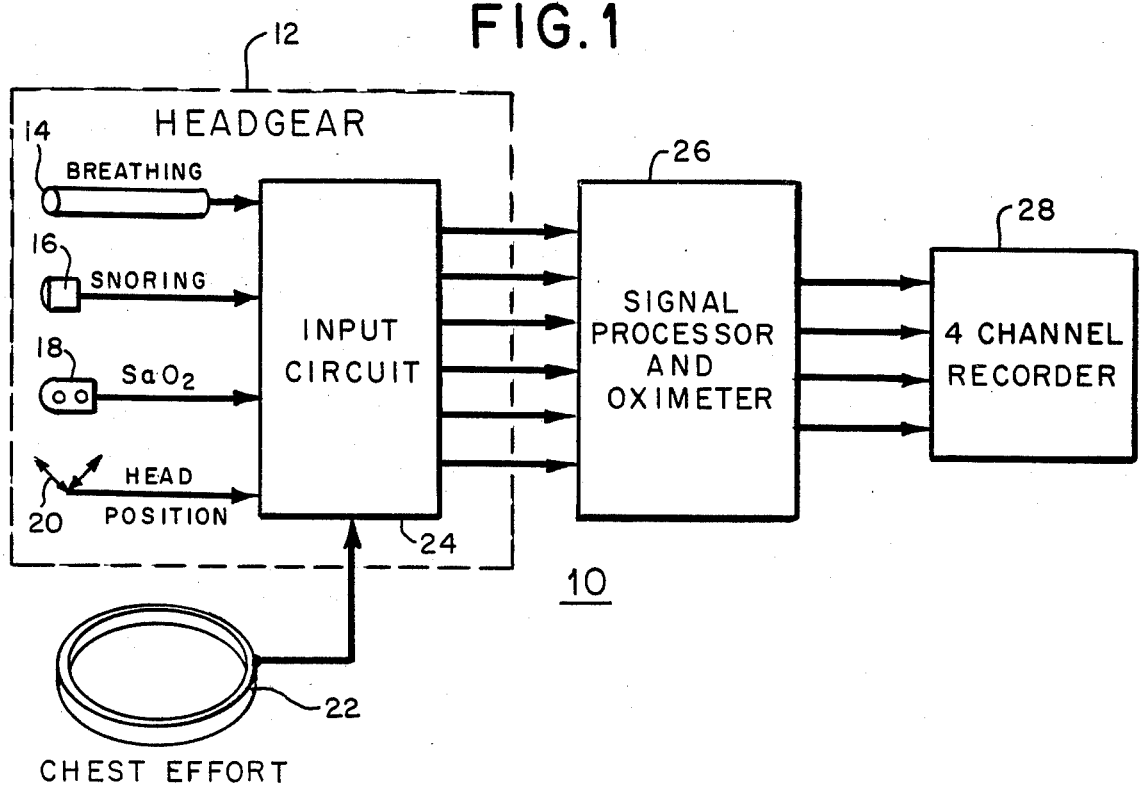
FIG. 1 is a block diagram of a first presently preferred embodiment of the monitor of this invention.

Turning now to the drawings, FIG. 1 shows a block diagram of a sleep apnea monitor 10 which incorporates a presently preferred embodiment of this invention. This monitor 10 includes a headgear 12 which fits on the head of a subject and contains a number of sensors. These sensors include a breathing sensor 14 which provides a signal to an input circuit 24 indicative of the breathing pattern of the subject. In addition, a snoring sensor 16 provides a signal to the input circuit 24 indicative of the snoring pattern of the subject. An $SaO_2$ sensor 18 optically measures the $SaO_2$ level at the forehead of the subject, and a pair of mercury switches cooperate to form a head position sensor 20 which provides an electrical signal indicative of the head position of the subject. In addition, the input circuit 24 receives a signal from a chest effort sensor 22 which is designed as a strap adapted to fit around the chest of the subject to indicate changes in the dimension of the chest of the subject. The purpose of the sensor 22 is to measure the effort being made by the subject to breathe, and in alternate embodiments the sensor may be placed on the torso of the subject either above or below the ribs.

As explained in greater detail below, the input circuit 24 preliminarily processes the sensor signals and displays indications of the state of the sensor signals. The preliminarily processed sensor signals are passed from the input circuit 24 to a signal processor 26 that includes an oximeter. As explained in detail below, the processor 24 further processes the sensor signals and generates output signals which are recorded on a conventional four-channel data recorder 2. In this embodiment, the four channels record breathing air flow as measured by the breathing sensor 14, chest movement as measured by the chest effort sensor 22, heart pulse waveform as measured by the $SaO_2$ monitor 18, and $SaO_2$ levels as measured by the $SaO_2$ monitor 18. In addition, the chest movement data channel also records information indicative the times when snoring is detected by the sensor 16, and the SaO$_2$ data channel also stores data indicative of the head position as measured by the sensor 20.

Figure 2:
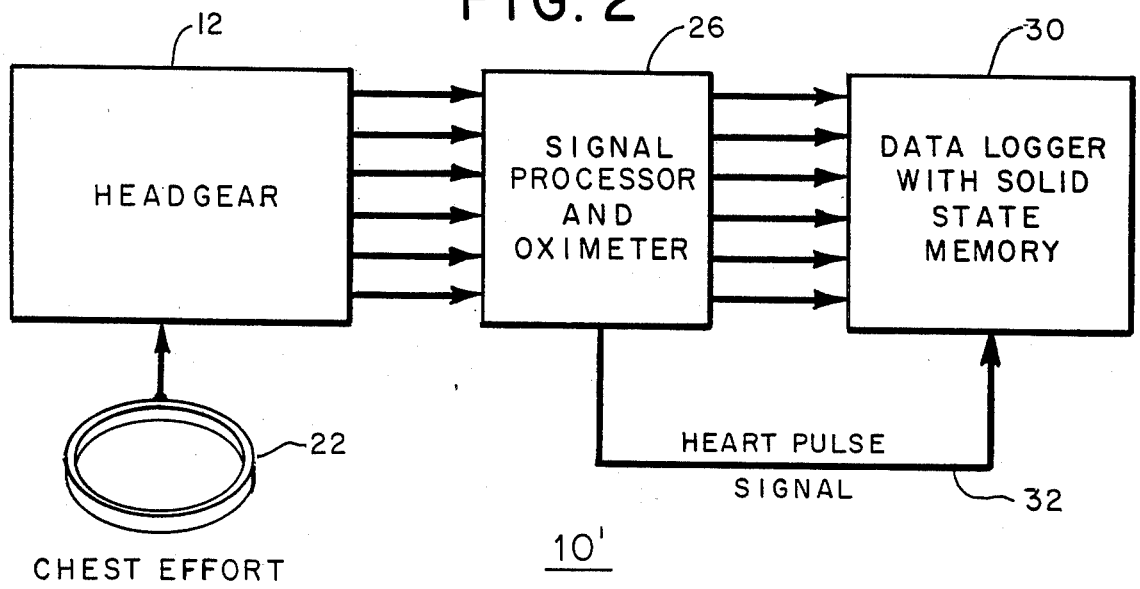
FIG. 2 is a block diagram of a second preferred embodiment of the monitor of this invention.

The precise manner in which the output signals from the signal processor 26 are used can vary widely in alternate embodiments of this invention. FIG. 2 shows one alternate in which the four-channel data recorder described above is replaced with a data logger 30 with solid state memory. This data logger 30 records the data on each of the respective channels at periodic intervals. According to this invention, the signal processor 26 generates a heart pulse signal on line 32 that is used to control the operation of the data logger 30. In particular, the data logger 30 records a set of data for each pulse of the subject as indicated by the heart pulse signal 32. By determining the recording rate of the data logger such that recordings are synchronized with pulse rate, it is insured that the sensors are consistently measured at the same phase angle of the pulse waveform. This allows pulse artifacts in the logged data to be eliminated. For example, the signal from the chest effort sensor 22 and the breathing sensor 14 may include components resulting from cardiac activity. By consistently logging the data at the same phase angle of the cardiac cycle, the cardiac component of the signal remains substantially constant and variations from measurement to measurement due to cardiac activity are reduced. Furthermore, by properly chosing the phase angle with respect to the cardiac cycle for each sensor, the component of the logged measurement attributable to cardiac activity can be maximized or minimized. In addition, the amount of memory required in the data logger 30 is reduced. In particular, each set of data is time stamped, and there is therefore no need to separately store information regarding pulse interval. Pulse interval information can be derived from the time stamps and can be used in analyzing fluctuations in pulse intervals.

In other alternates (not shown) the output signals from the signal processor 26 can be applied to an A/D converter for real time sampling and analysis by a computer system.

Turning now to FIGS. 3-16, these figures represent the presently preferred physical structure of the headgear 12. FIG. 3 is a perspective view of the headgear 12, and shows that the headgear includes first and second bands 40, 42. The first band 40 is positioned to extend around the head of the subject, across the forehead and over the ears. The second band 42 is secured to the first band 40 to extend over the top of the head of the subject. Both of the bands 40, 42 are provided with conventional adjusting mechanisms 44, 46 which allow the lengths of both of the bands 40, 42 to be adjusted. In many embodiments, the bands 40, 42 will be quite similar to the supporting harness of a helmet, and details of construction of the bands 40, 42 and the adjusting mechanisms 44, 46 can be varied widely. An elastic neck strap 50 extends downwardly from the first band 40 and is designed to fit under the chin of the subject to hold the headgear 12 properly in place.

The headgear 12 is interconnected with the signal processor 26 by means of a cable 48 which terminates in a junction block 66 positioned at the top of the second band 42. A pair of housings 62, 64 are fixedly mounted on respective sides of the second strap 42. These housings 62, 64 carry the input circuits, and are connected with the junction block 66 by means of cables 67.

The structure of the headgear 12 described above provides a stable support for the various sensors mounted on the headgear 12. By simply adjusting the lengths of the bands 40, 42, the headgear 12 can readily be adjusted to any particular subject. Once adjusted, the headgear 12 reliably and conveniently positions the various sensors properly on the head of the subject.

FIGS. 3-5 show the manner in which the SaO$_2$ sensor 18 is mounted in place. As shown in these figures, the headgear 12 includes an elastic forehead strap 52 which is secured at each end to the band 40 so as to confront the forehead of the user. Elastic loops 53 capture the strap 52 adjacent to the band 40 while allowing the strap 52 to move through the loops 53. A central portion of the forehead strap 52 carries a snap 54, and the SaO$_2$ sensor 18 carries a complimentary snap. The SaO$_2$ sensor 18 includes a set of LEDS 56 which are mounted adjacent to photodetectors 58. The LEDS 56 and photodetectors 58 are connected with the right housing 64 by means of a cable 60.

It has been found that reliable SaO$_2$ and pulse measurements can be made from the forehead of the subject. Reflection of light from the skull of the subject modifies the absolute levels of light received by the photodetectors 58. However, it is a simple matter to recalibrate conventional SaO$_2$ sensors to reliably measure SaO$_2$ levels at the forehead.

The structure described above provides a number of important advantages. First, the elastic forehead strap 52 insures that the SaO$_2$ sensor 18 is pressed against the forehead of the subject with an appropriate force to insure a reliable signal. Second, the SaO$_2$ sensor 18 responds quickly to changes in central SaO$_2$ levels because it is positioned at the forehead of the subject. It has been found that the forehead of the subject responds to changes in central SaO$_2$ levels substantially more quickly than extremities such as a fingertip commonly used for such measurements.

Turning now to FIGS. 6-14, the breathing sensor 14 includes a piezo-electric film 78 that is mounted in place in a generally cylindrical shape as shown in FIGS. 6-8. The structural assembly for the piezo-electric film 78 includes a central tube 68 which may, for example, be formed of a stiff, white vinyl tubing. Preferably, the central tube 68 defines an opening 70 (which may, for example, be ⅛ of an inch in diameter) and a pair of pressure relief grooves 72. A pair of cylindrical risers 74 are secured at each end of the tube 68 and these risers 74 can be formed of vinyl, for example (FIG. 9). An axially extending riser bar 76 is also secured to the central tube 68 as shown in FIGS. 10 and 11.

The riser 74 and the riser bar 76 support the piezo-electric film 78. It has been found preferable to insure that the piezo-electric film 78 is not in contact with the central tube 68 except at the risers 74 and the riser bar 76. In this way, approximately 80% of the piezo-electric film is out of contact with any supporting structure. This reduces the thermal inertia of the piezo-electric film 78 and improves responsiveness of the film. The piezo-electric film 78 supports first and second copper leads 80, one on each side of the film 78. The copper leads 80 are preferably held in place by a conductive adhesive. It may be preferable to provide small insulating elements such as elements 81 to prevent the conductive adhesive from moving to the other side of the film and shorting out the film. The film 78 is adhesively secured to the risers 74 and the riser bar 76, as, for example, with an adhesive such as 3-M Adhesive No. 468.

Following assembly, the piezo-electric film 78 and the remaining portions of the sensor 14 are spray coated with an insulating material to prevent shorting out of the piezo-electric film 78 in contact with the skin of the subject. Conductors 82 are then secured to the copper leads 80, and it is these conductors 82 which carry voltages generated by the piezo-electric film 78 in response to changes in temperature of the film 78.

After the conductors 82 have been positioned in place, first and second conduits 88, 90 are secured to the central tube 68, such that each of the conduits 88, 90 extends from a respective end of the central tube 68 (FIG. 12). The conduit 88 carries the conductors 82 to a connector 92, and the connector 92 is adapted for connection to a mating connector in the housing 62.

Once the conduits 88, 90 have been assembled with the central tube 68, vinyl wrapping tape 84 is used to cover the seams between the ends of the piezo-electric film 78 over the riser 74 and the circular end portions of the film 78 (FIG. 13). The adhesive described above has been found well-suited to hold the vinyl wrapping tape 84 in place. A pair of compression rings 86 (formed, for example, of silicone rubber) are then slipped on each end over the seam covering tape 84 (FIG. 13). These compression rings 86 exert constant pressure on the piezo-electric film 78 and also provide a mechanical bond between the piezo-electric film 78 and the copper leads 80. Then a closed cell support bar 79 is adhesively secured to the film 78 over the riser bar 76. The support bar 79 performs three important functions: (1) it centers the sensor 14 on the upper lip of the subject; (2) it reduces discomfort of the subject; and (3) it enhances the selectivity of the snoring sensor 16 to snoring sounds.

In order to complete assembly, a deflector plate 100 which includes an array of openings 102 is snapped in place about the conduits 88, 90 in alignment with the piezo-electric film 78. As shown in FIG. 4, this deflector plate 100 acts to deflect exhaled air from the mouth of the subject towards the piezo-electric film of the sensor 14. The openings 102 reduce the amount of exhaled air that is redirected back against the face of the subject, and are not required in all embodiments. Because the plate 100 snaps in place, it can readily be adjusted and removed for cleaning.

As shown in FIGS. 6 and 15 the conduit 90 acoustically couples the interior of the central tube 68 to a tube 94 that is secured to the right housing 64. This tube 94 terminates in a sound cone 96 that directs sound from the conduit 90 to a microphone 98 mounted within the right housing 64. The separation between the sound cone 96 and the microphone 98 can be ajusted for proper coupling between the two. In this embodiment a separation of ¼ centimeter has been found to provide consistent, stable results.

In use, the breathing sensor 14 is positioned properly in place immediately under the nose of the subject after the bands 40, 42 have been adjusted to length properly. The breathing sensor 14 is held in place by the conduits 88, 90 which function as support tubes. The conduits 88, 90 are releasibly clamped in place to the band 40 by respective channels 104 (FIGS. 4 and 4a). By simply removing the conduits 88, 90 from the channels 104 and then repositioning the conduits 88, 90 in the channels 104, the effective lengths of the conduits 88, 90 can be varied in order to position the breathing sensor 14 as needed. In addition, the channels 104 allow easy adjustment of the rotational position of the conduits 88, 90 and therefore of the sensor 14.

The piezo-electric film 78 of the breathing sensor 14 generates voltages in response to temperature changes of the film 78. The piezo-electric film marketed by the Penwalt Corporation under the trade name Kynar has been found to be suitable. In use, exhaled air from the subject raises the temperature of the piezo-electric film 78 which, in turn, generates voltages on the conductors 82 that are processed as described below. The deflector plate 100 insures that air exhaled through the mouth of the patient is directed toward the piezo-electric film 78, and the placement of the breathing sensor 14 insures that air exhaled out of the nostrils of the subject also contacts the piezo-electric film 78.

The piezo-electric film 78 provides a number of important operating advantages. First, it is a relatively large area sensor, and for this reason it can be used to monitor exhaled air from the both the mouth and the nostrils of the subject. Second, this film 78 does not require calibration or any warm-up period. In addition, because the film 78 is responsive to temperature changes characteristic of exhaled air, air currents in the room will not generate artifacts in signal generated by the film 78. Finally, because the film 78 is not positioned at the mouth of the subject, the breathing sensor 14 does not produce an erroneous signal when the subject opens his mouth without breathing. This is a significant advantage over prior art thermistor breath sensors which can produce an erroneous signal in this situation.

The snoring sensor 16 utilizes the cavity defined by the piezo-electric film 78. In effect, the cavity defined by the piezo-electric film 78 is a resonant cavity which is acoustically coupled to the microphone 98 by the conduit 90. The electric signal generated by the microphone 98 can readily be used to indicate whether or not the subject is snoring. It has been found that the pressure relief grooves 72 reduce the sounds of breathing, and the grooves 72 and the opening 70 improve responsiveness to snoring sounds.

The piezo-electric film 78 described above has characteristic striations. It has been found that the breathing sensor 14 can function with these striations arranged either to run around the circumference of the breathing sensor 14 or to run axially along the length of the breathing sensor 14. In preliminary tests, it appears that the film 78 provides an increased signal level when the striations run around the circumference of the breathing sensor 14, while the film provides more consistent signal levels when the striations run along the length of the sensor 14.

The chest effort sensor 22 can be formed of a chest band which includes a piezo-electric film similar to that described above which responds to increases in chest dimension by generating electrical voltages that are applied as an input to the input circuit 24. The head position sensor 20 can be formed of a pair of mercury switches arranged at an angle with respect to one another so as to indicate the spatial orientation of the headgear 12 and therefore of the head of the subject.

Figure 16:
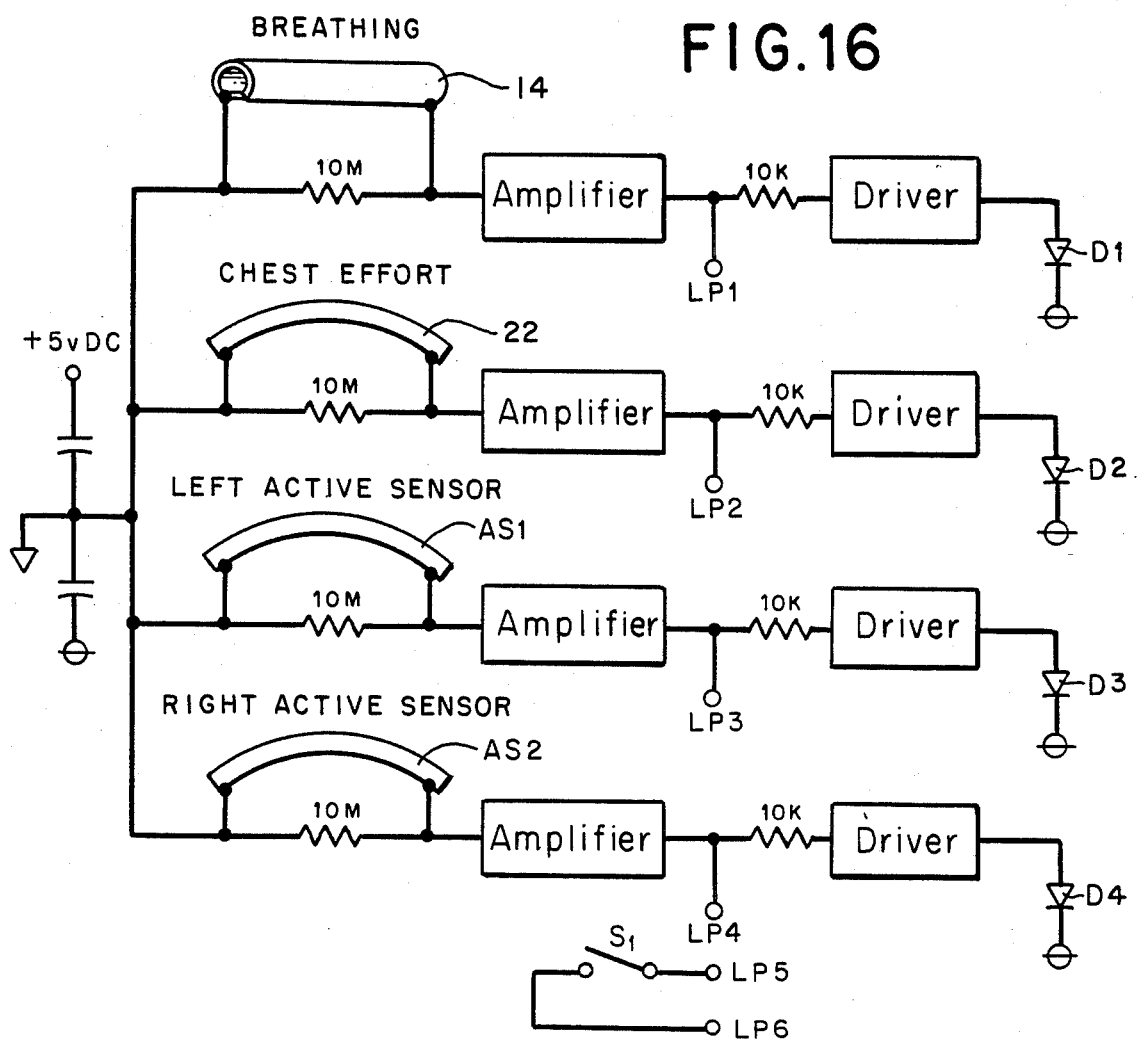
FIGS. 16, 16A, 16B, 17 and 17A are circuit diagrams of the input circuit of FIG. 1.
Figure 16A:
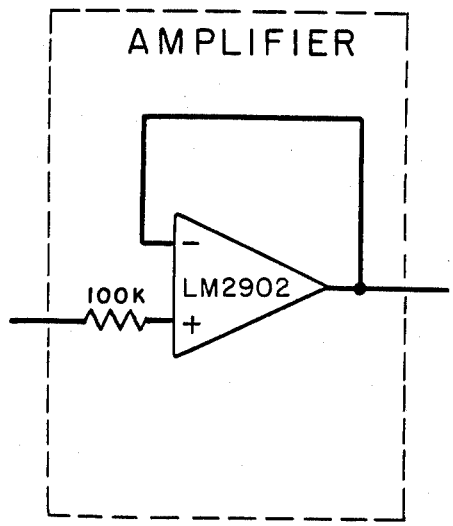
Figure 16B:
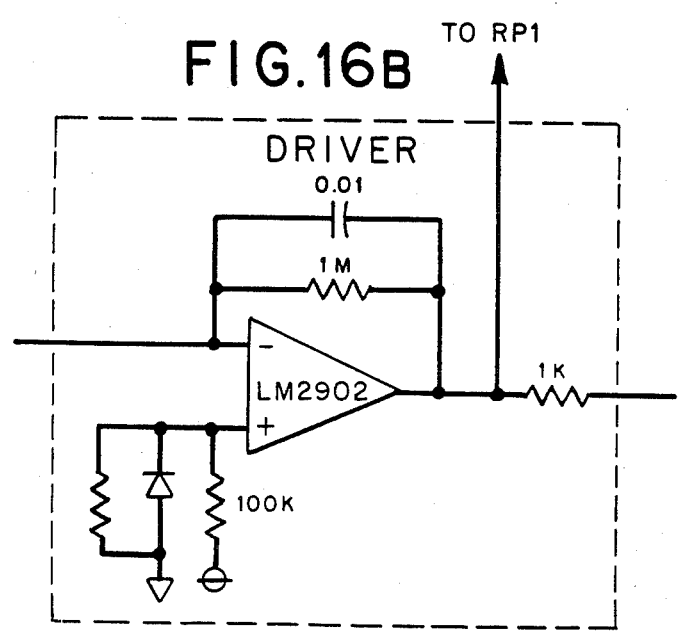
Figure 17:
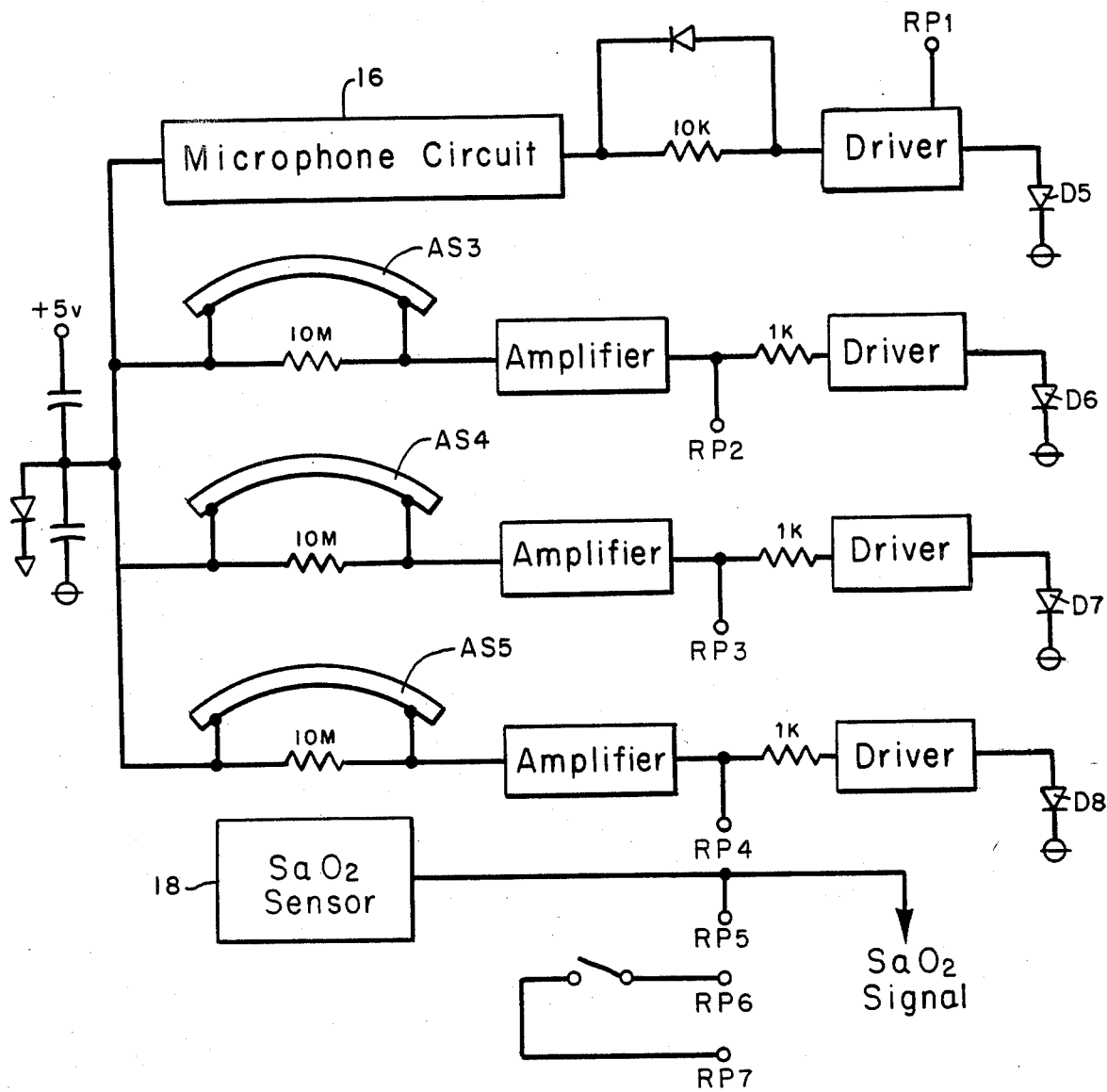

FIGS. 16–18B show detailed drawings of the electronic circuitry of the input circuit 24 and the signal processor 26 described above. FIGS. 16 and 17 show block diagrams of the circuitry contained in the housings 62, 64, respectively. As shown in FIG. 16, the circuitry of the left housing 62 includes LEDS D1–D4. The breathing and chest effort sensors 14, 22 generate voltages which are amplified and then passed to the signal processor 26 via terminals LP1, LP2. These signals are also used to drive the LEDS D1, D2 via the drivers shown. The housing 62 has been configured for an expanded system which includes additional sensors in addition to those described above. The diodes D3, D4 and the terminals LP3, LP4 are used in conjunction with left and right active sensors AS1, AS2. These sensors AS1, AS2 can, for example, include piezo-electric film straps adapted to be positioned around the hand and calf, respectively, of the subject. Waking of a subject is typically associated with reflexive gripping actions in the hand or movements of the foot. The left and right active sensors AS1, AS2 can be used to detect such indications of waking. FIGS. 16A and 16B show detailed schematic diagrams of suitable amplifiers and drivers.

Figure 17A:
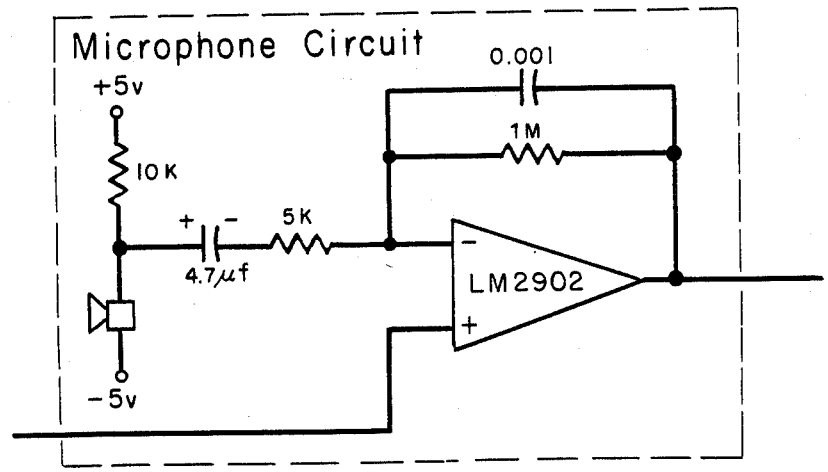

FIG. 17 shows a block diagram of the circuitry of the right housing 64. This right housing 64 includes a microphone circuit as shown in FIG. 17A which includes the microphone 98. As before, drivers are used to drive LEDS D5-D8 to indicate the state of the respective sensor signals. The housing 64 provides three auxiliary channels for additional sensors AS3-AS5, shown in FIG. 17 as respective piezo-electric strips. The amplifiers and drivers of FIG. 17 can be those shown in FIGS. 16A and 16B, respectively. In addition, the signals from the $SaO_2$ sensor 18 are routed through the right housing 64.

The head position sensor 20 includes two mercury switches $S_1$, $S_2$, each mounted in a respective one of the housings 62, 64. The two switches $S_1$, $S_2$ are oriented with respect to each other such that the pattern of switch closures indicates the position of the head of the subject.

By watching the blinking patterns of the diodes D1-D8 it is possible to determine whether the respective sensors are functioning properly. The diodes D1-D8 have been found to aid in sensor placement and to improve confidence of the subject. During set up, the subject can be asked to breathe normally and the appropriate ones of the diodes D1-D8 can be watched to confirm proper sensor placement and operation.

Figure 18:
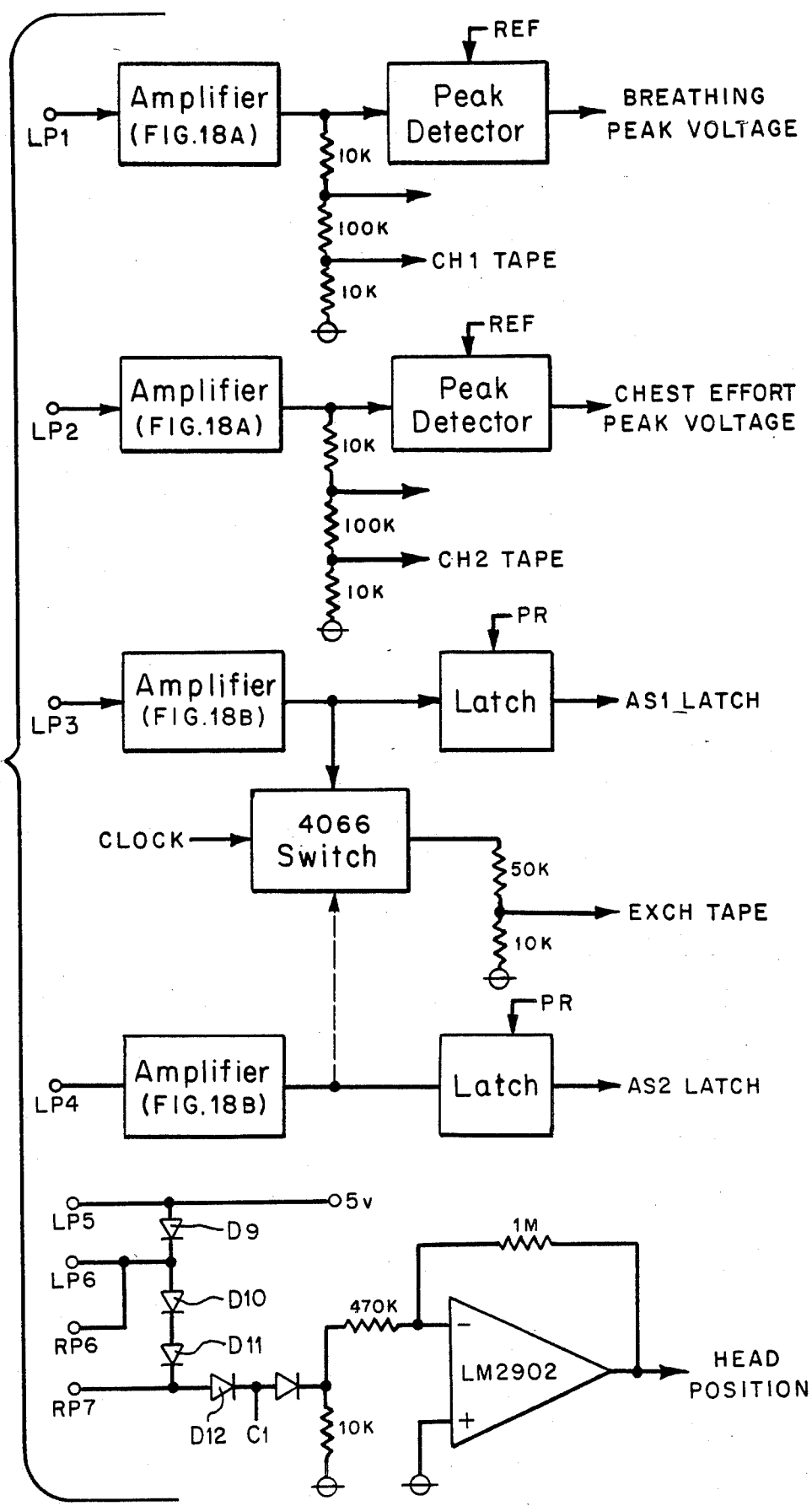

FIG. 18 shows a block diagram of the portion 26L of the signal processor 26 which relates to signals generated by the left housing 62. As shown in FIG. 18, the breathing sensor signal is supplied via terminal LP1 to an amplifier, and the analog amplified value is then applied to Channel 1 of the four-channel recorder 28. In addition, the amplified breathing sensor signal is supplied to a peak detector which samples and holds the peak voltage generated by the breathing sensor 14 during each exhalation of the subject. Alternately the breathing sensor signal can be processed to monitor inhalation of the subject.

Figure 18A:
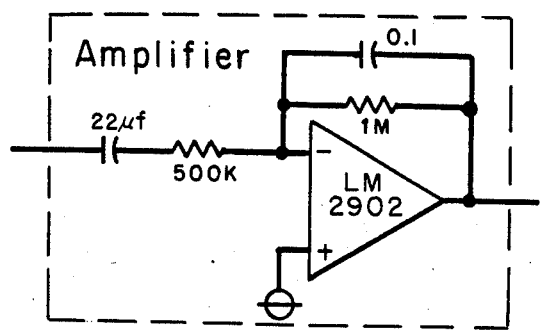
Figure 18B:
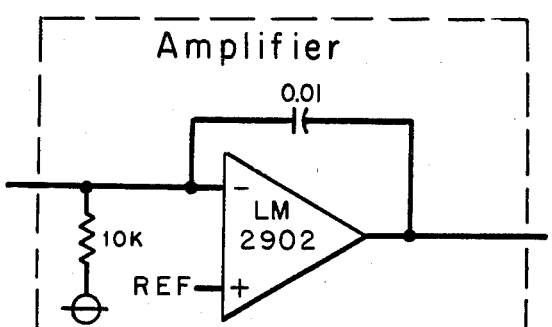
Figure 18C:
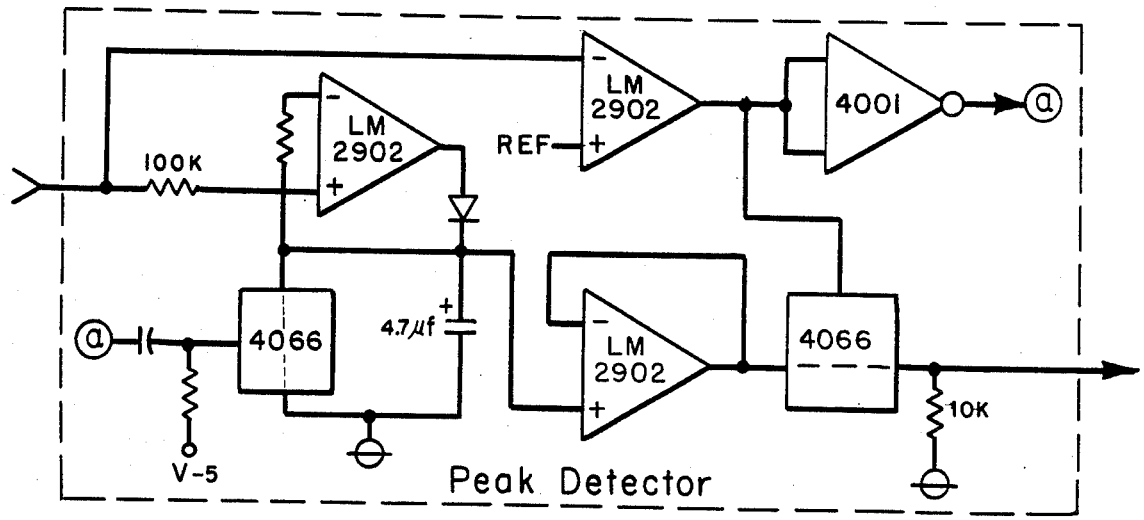
Figure 18D:
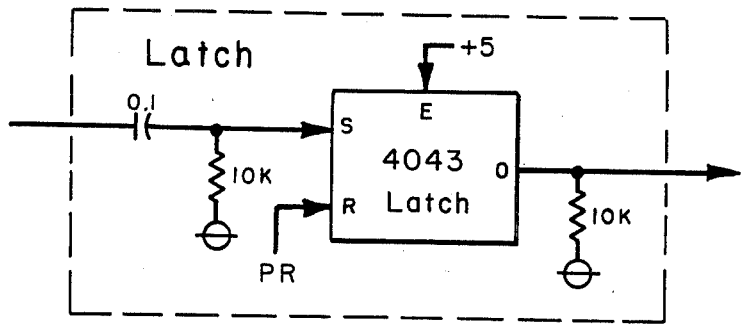
Figure 18E:
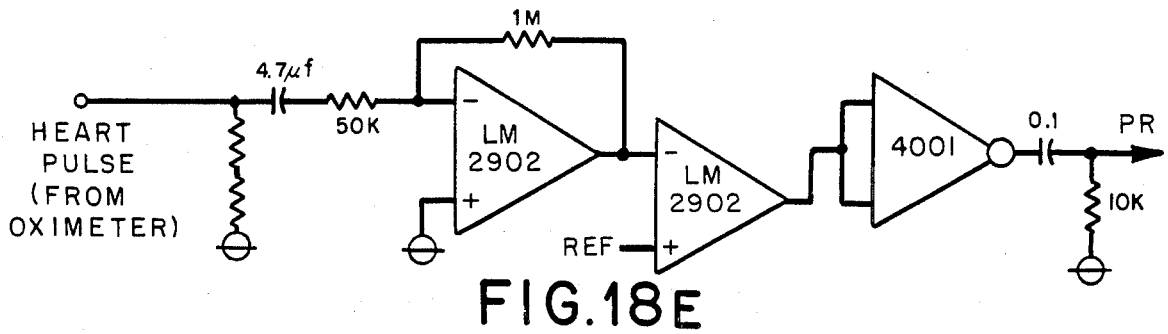

Similarly, the chest effort sensor signal on terminal LP2 is amplified, and the amplified signal is recorded on Channel 2 of the four-channel recorder 28. Channel 2 allows central apnea events and obstructive apnea events to be distinguished from one another. The peak value of the amplified chest effort signal is also detected for each inhalation of the subject. The signals from the left and right active sensors AS1, AS2 appearing on terminals LP3, LP4 are amplified, and the amplified values are then used to control a solid state switch which receives as an input a 40 Hz modulated signal. When either the left or right active sensor generates a signal, the modulated signal is passed via the switch to another channel of the tape. The 40 Hz modulated signal is not essential for all applications. For example, the data logger 30 records actual signal levels, and there is no need to use a modulated signal such as the 40 Hz signal in the embodiment of FIG. 2, In addition, the amplified outputs of the left and right active sensors are stored by latches. These latches are reset by the signal PR once each heart pulse of the subject and the latches are set at any time by the presence of an amplified signal from the respective active sensor. In the embodiment of FIG. 2, the data logger 30 is controlled to store the states of the latches once per heart pulse of the subject immediately before the latches are reset by the signal PR. FIGS. 18A and 18B provide schematic diagrams for suitable amplifier circuits; FIG. 18C shows a schematic diagram for a suitable peak detector circuit; and FIG. 18D shows a schematic diagram for a suitable latch circuit. The heart pulse signal PR can be generated from the oximeter with the circuit shown in FIG. 18E.

As shown in FIG. 18, the signal processor 26 includes a set of diodes D9-D12. The head position sensor 20 includes two mercury switches $S_1$, $S_2$ which are arranged to short the diode D9 and the diodes D10, D11, respectively. The output signal on line C1 will thus be five volts DC decreased by one diode drop when both of the switches $S_1$, $S_2$ are closed, decreased by two diode drops when only the switch $S_2$ is closed, decreased by three diode drops when only the switch $S_1$ is closed and decreased by four diode drops when none of the switches $S_1$, $S_2$ is closed. Thus, the voltage on the line C1 provides an indication of the state of the head position sensor 20. The voltage on line C1 is amplified and is then superimposed as described above on the oximetric signal channel of the four-channel recorder.

FIG. 19 shows the portion 26R of the signal processor 26 associated with the right housing 64. The signal from the snoring sensor 16 on terminal RP1 is processed to control a solid state switch such that the switch passes a 40 Hz modulated signal when snoring is detected and it blocks the clock signal when snoring is not detected. This switched modulated signal can be applied to the chest effort tape Channel 2 so as to superimpose the snoring measurement on the chest effort measurement.

The terminals RP2, RP3 and RP4 as described above receive signals from additional active sensors which are processed, depending upon the sensor, either with by means of a peak detector or a latch as described above.

The terminal RP5 receives the signal from the $SaO_2$ sensor 18, which is applied to a conventional oximeter, such as Criticare Systems, Inc. Model 501+. The oximeter generates a pulse waveform which is applied to Channel 3 of the tape and an $SaO_2$ signal which is used to generate a pulse width modulated signal that is applied to Channel 4 of the tape.

The remaining figures show additional circuitry utilized in the block diagrams described above. In particular, FIG. 19A shows a circuit used to generate the reference signal REF, and FIG. 19B shows a suitable power supply.

CONCLUSION

The foregoing description relates to a sleep apnea monitor which provides a number of important advantages. This monitor can be adjusted simply and quickly to fit any particular subject, and once adjusted it can easily be removed and replaced by the subject while maintaining proper sensor placement. This monitor is convenient to use and wear because most of the sensors are positioned on the head of the subject. As pointed above, this placement of sensors also improves monitor operation. The cylindrical shape of the breathing sensor provides structural support to the piezo-electrical film without increasing thermal inertia. unacceptably, and this cylindrical shape allows the piezo-electric film to be used as part of the resonant chamber that is coupled to the microphone of the snoring sensor.

Of course, it should be understood that the preferred embodiments described above can readily be modified. For example, the conduits 88, 90 can be positioned closer to the nose of the subject to reduce the interference of the conduits with sleeping of the subject. Furthermore, the various features of this invention can be used separately rather than in combination as described above.

It is therefore intended that the foregoing detailed description be regarded as illustrative rather than limiting, and that it be understood that it is the following claims, including all equivalents, which are intended to define the scope of this invention.

I claim:

1. A sensor positioning device for an oximeter of the type comprising an emitter having at least one light source, a receiver having at least one photosensor, and means for monitoring the receiver to measure selected body parameters, said device comprising:
   a headband configured to rest on the head of a subject;
   means for mounting the emitter and the receiver to the headband in side-by-side relationship such that both the emitter and the receiver are directed toward the forehead of the subject;
   means, included in the mounting means, for resiliently biasing the emitter and receiver into contact with the forehead of the subject;
   a breath sensor; and
   means for mounting the breath sensor to the headband to position the breath sensor to respond to air exhaled by the subject.

2. The invention of claim 1 wherein the mounting means mounts the breath sensor between the nose and mouth of the subject.

3. The invention of claim 1 wherein the breath sensor mounting means comprises:
   at least one conduit mounted to the breath sensor; and
   at least one channel mounted on the headband to removably and adjustably clamp the conduit in place such that the effective length of the conduit and the position of the breath sensor can be adjusted by repositioning the conduit in the channel.

4. The invention of claim 1 wherein the breath sensor comprises:
   a piezo-electric film;
   means for supporting the film in a cylindrical shape;
   a first tube which extends between the film supporting means and the headband; and
   at least one conductor which extends from the piezo-electric film to the headband.

5. The invention of claim 4 wherein the breath sensor further comprises a resilient member mounted to the film to center the cylindrical shape on the upper lip of the subject.

6. The invention of claim 4 further comprising a snoring sensor comprising:
   a microphone mounted to the headband;
   conduit means for conducting sound from a region within the cylindrical shape of the piezo-electric film to the microphone.

7. The invention of claim 6 wherein the conduit means comprises;
   a first tube mounted coaxially within and spaced from the piezo-electric film, said first tube defining an opening in a side wall of the first tube, and
   a conduit mounted between the microphone and the first tube.

8. The invention of claim 7 further comprising a channel mounted to the headstrap and sized to adjustably and releasibly secure the conduit to the headband such that the effective length of the conduit, and therefore the position of the breath sensor, can be adjusted by repositioning the conduit in the channel.

9. The invention of claim 1 wherein the breath sensor comprises:
   a piezo-electric film;
   means for mounting the film in a cylindrical shape, and
   means for deflecting exhaled air from at least one of the mouth and nostrils of the subject against the film such that the film responds to air exhaled by the patient through both the mouth and the nostrils.

10. The invention of claim 9 wherein the deflecting means comprises a plate positioned to deflect air exhaled by the subject through the mouth toward the piezo-electric film.

11. The invention of claim 10 wherein the plate is perforated to reduce redirection of exhaled air back toward the subject.

12. The invention of claim 1 further comprising:
    means, mounted to the headband, for generating at least one electrical signal indicative of spatial orientation of the headband.

13. The invention of claim 12 further comprising:
    means, electrically coupled to the headband, for sensing chest movement of the subject.

14. A sensor positioning device for an oximeter of the type comprising an emitter having at least one light source, a receiver having at least one photosensor, and means for monitoring the receiver to measure selected body parameters, said device comprising:
    a headband configured to rest on the head of a subject;
    means for mounting the emitter and the receiver to the headband in side-by-side relationship such that both the emitter and the receiver are directed toward the forehead of the subject;
    means, included in the mounting means, for resiliently biasing the emitter and receiver into contact with the forehead of the subject;
    a first strap positioned to encircle the head of the subject at the forehead;
    a second strap secured to the first strap to extend over the top of the head of the user; and
    means for adjusting the lengths of the first and second straps.

15. The invention of claim 14 further comprising a resilient chin strap secured to the headband and configured to extend under the chin of the subject.

16. A health parameter sensing and data logging system comprising:
    a plurality of sensors, each comprising means for sensing a respective health parameter and for generating a respective signal indicative of said parameter;

means for processing the signals;

means for logging the processed signals at selected intervals in response to an activation signal; and means for generating the activation signal in synchronization with the heart pulse of a subject such that the processed signals are logged in synchronization with the heart pulse.

17. A sensor positioning device for an oximeter of the type comprising an emitter having at least one light source, a receiver having at least one photosensor, and means for monitoring the receiver to measure selected body parameters, said device comprising:

a headband configured to rest on the head of a subject;

means for mounting the emitter and the receiver to the headband in side-by-side relationship such that both the emitter and the receiver are directed toward the forehead of the subject, said mounting means comprising:

an elastic strap having first and second ends and an intermediate section;

means for securing the first and second ends of the strap to the headband such that the strap is positioned on a chord of the headband; and means for securing the emitter and receiver to the intermediate section;

said strap dimensioned to bias the emitter and receiver against the forehead of the subject.

* * * * *